United States Patent
Kato

(10) Patent No.: US 9,826,909 B2
(45) Date of Patent: Nov. 28, 2017

(54) NEUROGENIC BAROREFLEX SENSITIVITY MEASUREMENT DEVICE, NEUROGENIC BAROREFLEX SENSITIVITY MEASUREMENT PROGRAM AND NEUROGENIC BAROREFLEX SENSITIVITY MEASUREMENT METHOD

(71) Applicant: SAPPORO MEDICAL UNIVERSITY, Sapporo-shi, Hokkaido (JP)

(72) Inventor: Yuichi Kato, Sapporo (JP)

(73) Assignee: SAPPORO MEDICAL UNIVERSITY, Sapporo-shi, Hokkaido (JP)

(*) Notice: Subject to any disclaimer, the term of this patent is extended or adjusted under 35 U.S.C. 154(b) by 98 days.

(21) Appl. No.: 14/775,827

(22) PCT Filed: Mar. 28, 2014

(86) PCT No.: PCT/JP2014/059081
§ 371 (c)(1),
(2) Date: Sep. 14, 2015

(87) PCT Pub. No.: WO2014/157605
PCT Pub. Date: Oct. 2, 2014

(65) Prior Publication Data
US 2016/0029909 A1   Feb. 4, 2016

(30) Foreign Application Priority Data

Mar. 29, 2013  (JP) ................................. 2013-074027

(51) Int. Cl.
*A61B 5/02*  (2006.01)
*A61B 5/021*  (2006.01)
(Continued)

(52) U.S. Cl.
CPC ........ *A61B 5/02125* (2013.01); *A61B 5/0261* (2013.01); *A61B 5/02416* (2013.01);
(Continued)

(58) Field of Classification Search
CPC ............ A61B 5/02125; A61B 5/02416; A61B 5/0261; A61B 5/4035; A61B 5/7246
See application file for complete search history.

(56) References Cited

U.S. PATENT DOCUMENTS

| 2003/0216652 | A1 | 11/2003 | Narimatsu et al. |
| 2009/0124914 | A1* | 5/2009 | Kuo .................. A61B 5/02116 600/500 |
| 2010/0004546 | A1* | 1/2010 | Tanaka .............. A61B 5/02007 600/485 |

FOREIGN PATENT DOCUMENTS

| JP | 2004-41244 A | 2/2004 |
| JP | 2008-86568 A | 4/2008 |

(Continued)

OTHER PUBLICATIONS

Brian E. Hunt et al: Quantification of Mechanical and Neural Components of Vagal Baroreflex in Humans, Hypertension vol. 37, Issue. 6, 2001, pp. 1362-1368.
(Continued)

*Primary Examiner* — Robert N Wieland
(74) *Attorney, Agent, or Firm* — Muncy, Geissler, Olds & Lowe, P.C.

(57) ABSTRACT

[Problem] To provide a neurogenic baroreflex sensitivity measurement device, neurogenic baroreflex sensitivity measurement program and neurogenic baroreflex sensitivity measurement method capable of easily and objectively measuring neurogenic baroreflex sensitivity that is not dependent on vascular hardness without using blood pressure or pulsations in the diameter of the carotid artery.

(Continued)

[Solution] The neurogenic baroreflex sensitivity measurement device comprises: a pulse wave data-acquiring unit (41) for acquiring pulse wave data of an artery; a normalized pulse wave volume-calculating unit (42) for calculating a normalized pulse wave volume on the basis of the pulse wave data; a pulse interval-acquiring unit (43) for acquiring pulse intervals corresponding to the pulse wave data; a baroreflex series-detecting unit (44) for detecting baroreflex series in which the normalized pulse wave volume and pulse interval both increase or decrease for at least three beats in a row; and a neurogenic baroreflex sensitivity-calculating unit (45) for calculating the slope of a regression line representing the correlation between the normalized pulse wave volume and the pulse interval in a baroreflex series as the neurogenic baroreflex sensitivity, which is an index representing the neurogenic baroreflex function.

6 Claims, 10 Drawing Sheets

(51) Int. Cl.
   *A61B 5/00* (2006.01)
   *A61B 5/024* (2006.01)
   *A61B 5/026* (2006.01)

(52) U.S. Cl.
   CPC .......... *A61B 5/4035* (2013.01); *A61B 5/7246* (2013.01); *A61B 5/7278* (2013.01); *A61B 5/7264* (2013.01); *A61B 5/7275* (2013.01); *A61B 2562/0238* (2013.01)

(56) References Cited

FOREIGN PATENT DOCUMENTS

JP      2011-189080 A      9/2011
WO      2008/105229 A1     9/2008

OTHER PUBLICATIONS

Masashi Ichinose et al.: Modulation of arterial baroreflex dynamic response during mild orthostatic stress in humans, The Journal of Physiology vol. 557, Issue. 1, 2004, pp. 321-330.
International Search Report of PCT/JP2014/059081.
Paola Martínez-García et al, Relation of the baroreflex mechanism with the photoplethysmo-graphic volume in healthy humans during orthostatism, Arch Cardiol Mex, (2012), p. 82-90.
Sawada Y et al, Normalized pulse volume (NPV) derived photoplethysmographically as a more valid measure of the finger vascular tone, International Journal of Psychophysiology, Elsevier, Amsterdam, NL, vol. 41, No. 1, pp. 1-10.

* cited by examiner

[FIG. 1]
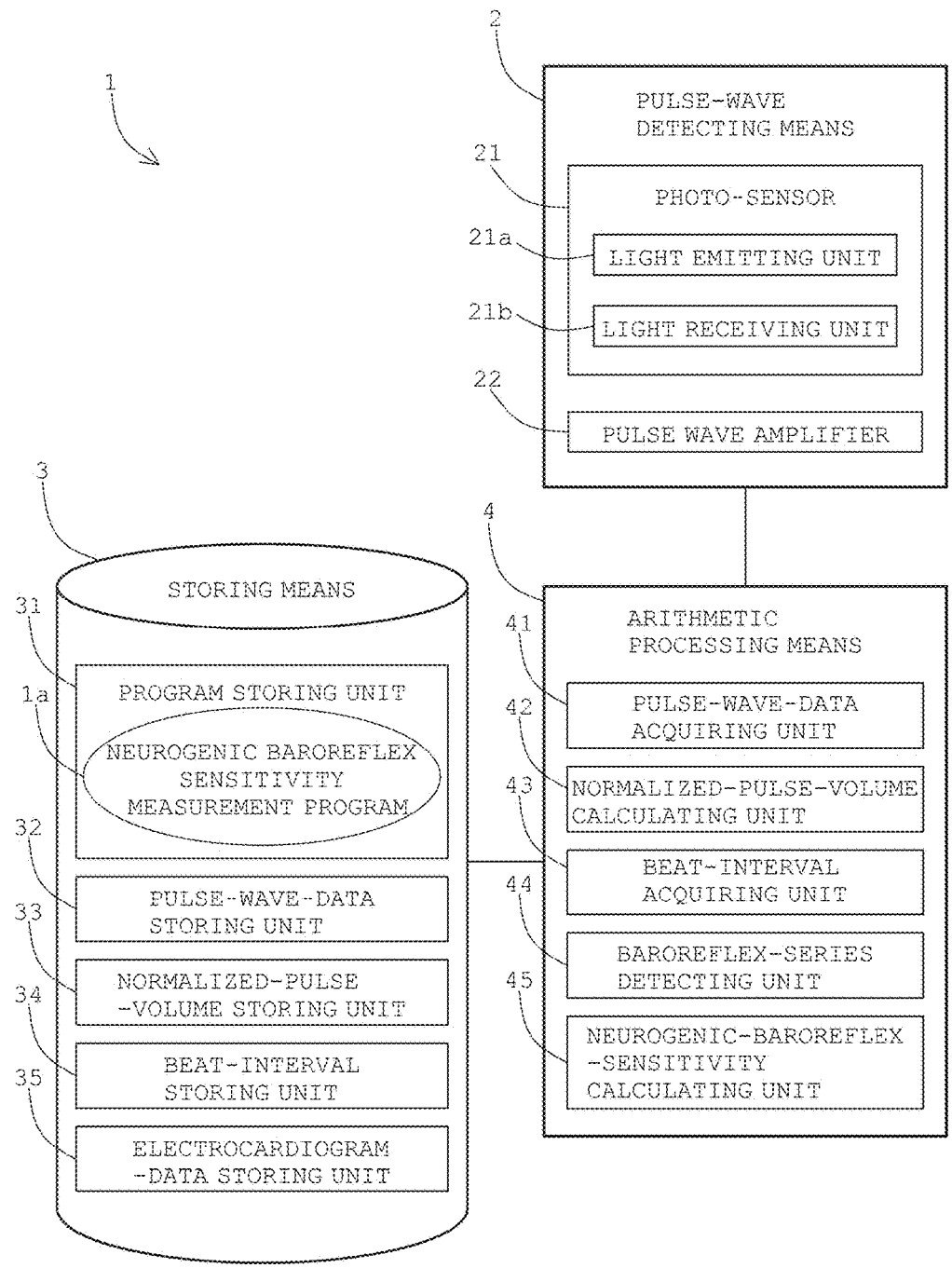

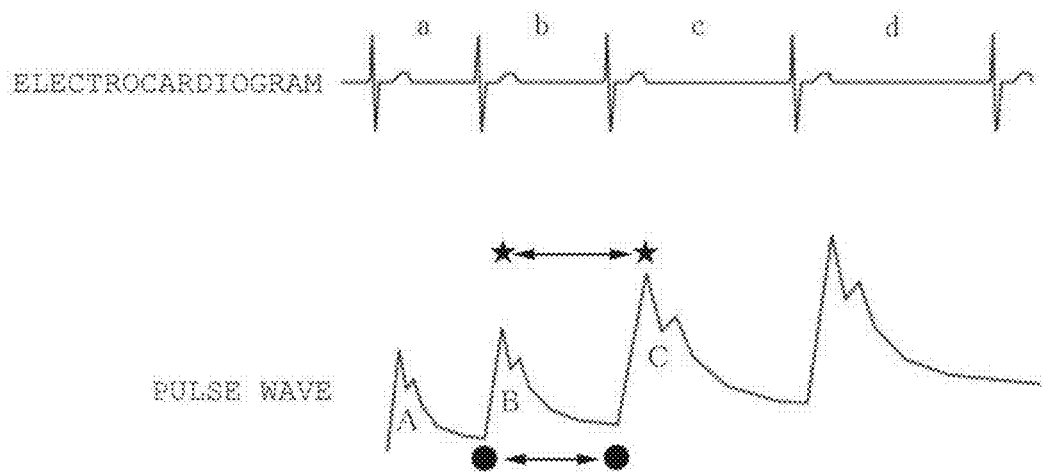
[FIG. 2]

[FIG. 3]
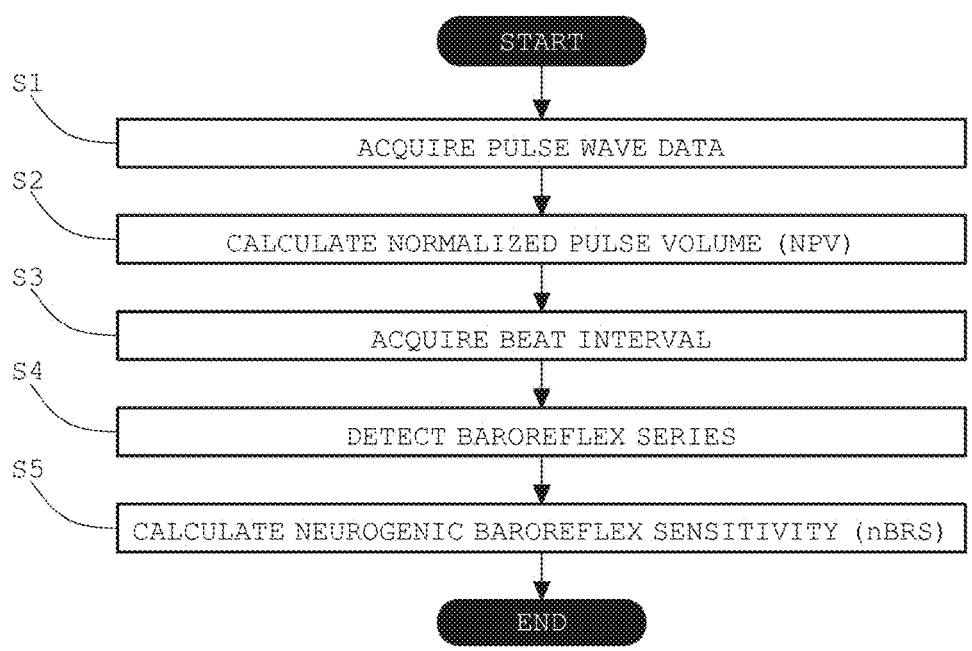

[FIG. 4A]
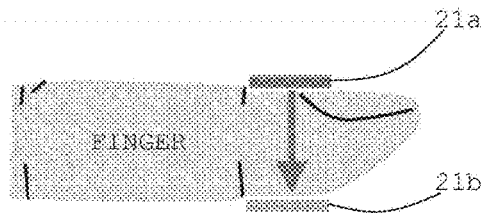
[FIG. 4B]
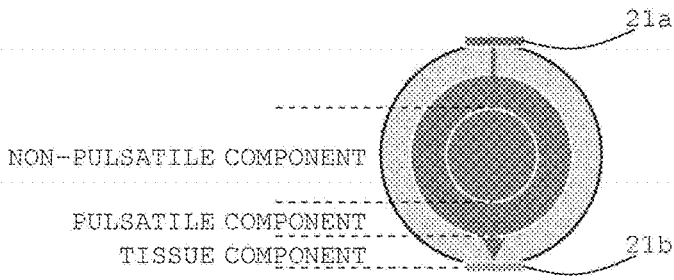
[FIG. 4C]
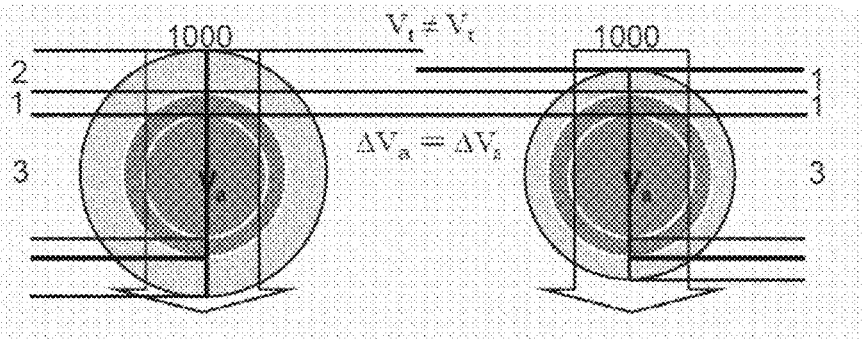

[FIG. 5A]
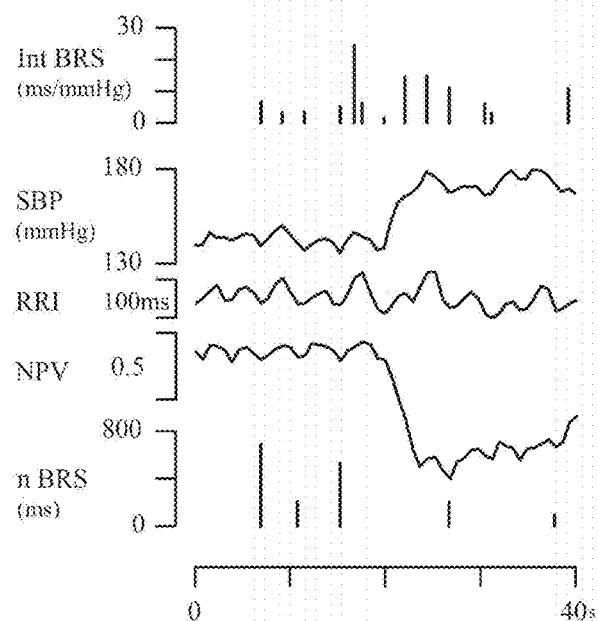
[FIG. 5B]
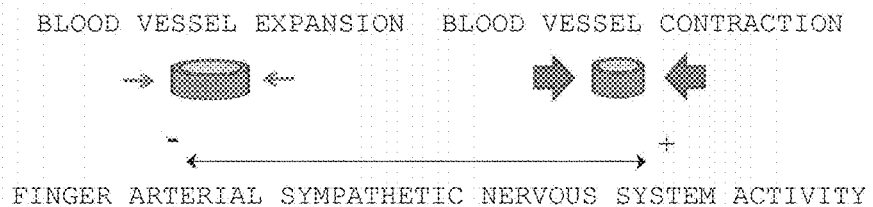
[FIG. 5C]
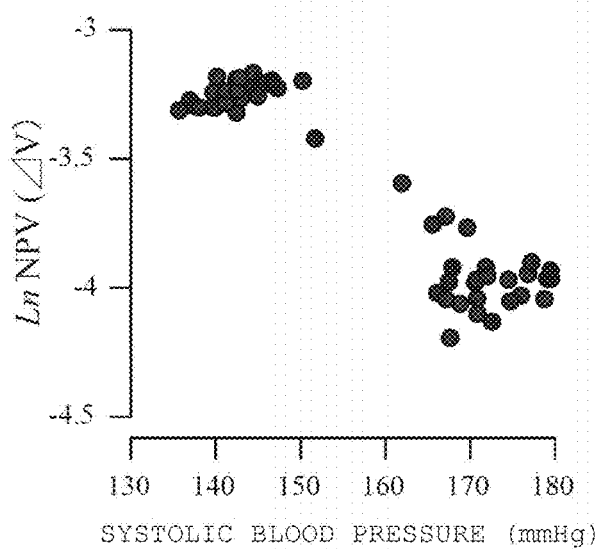

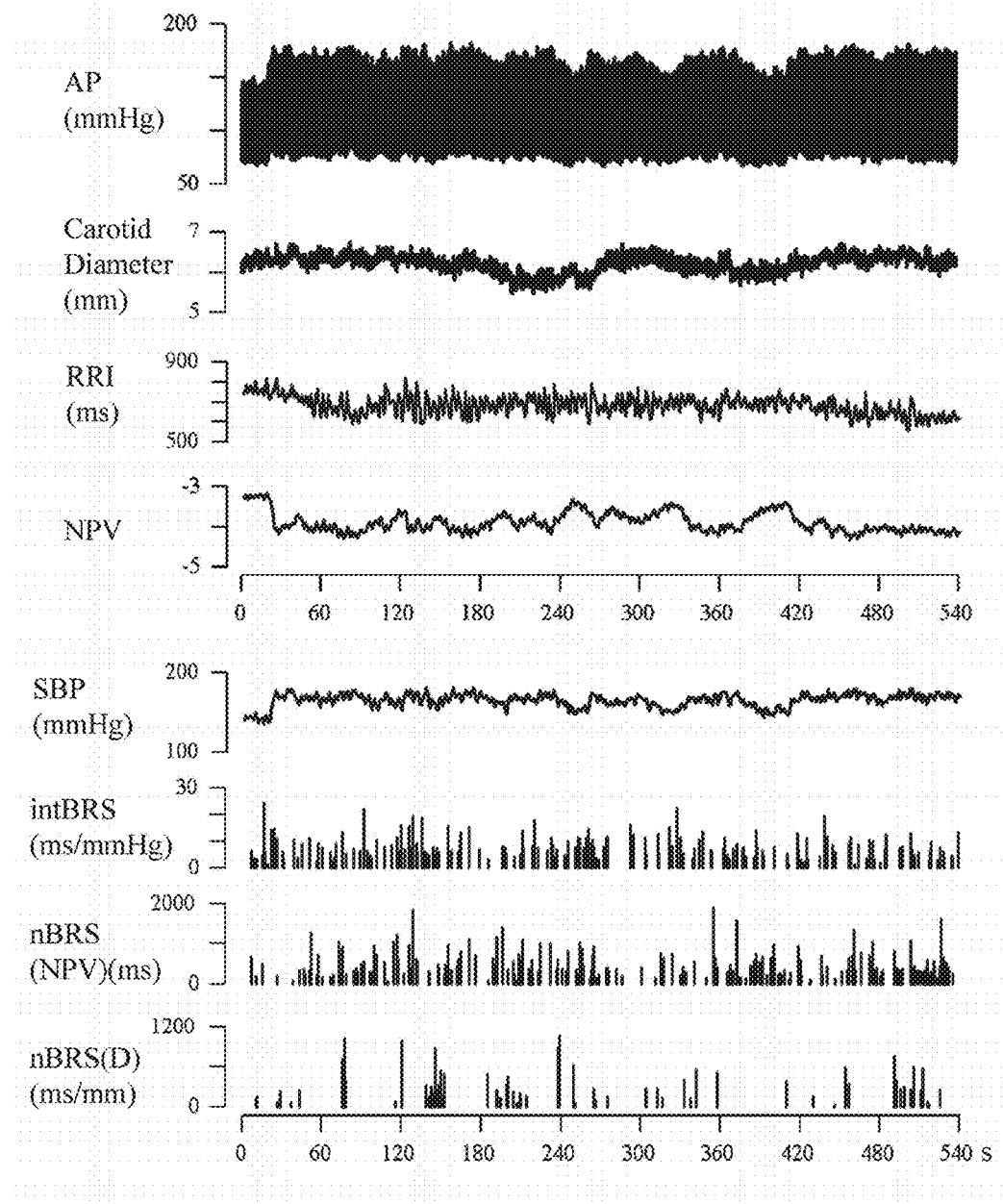

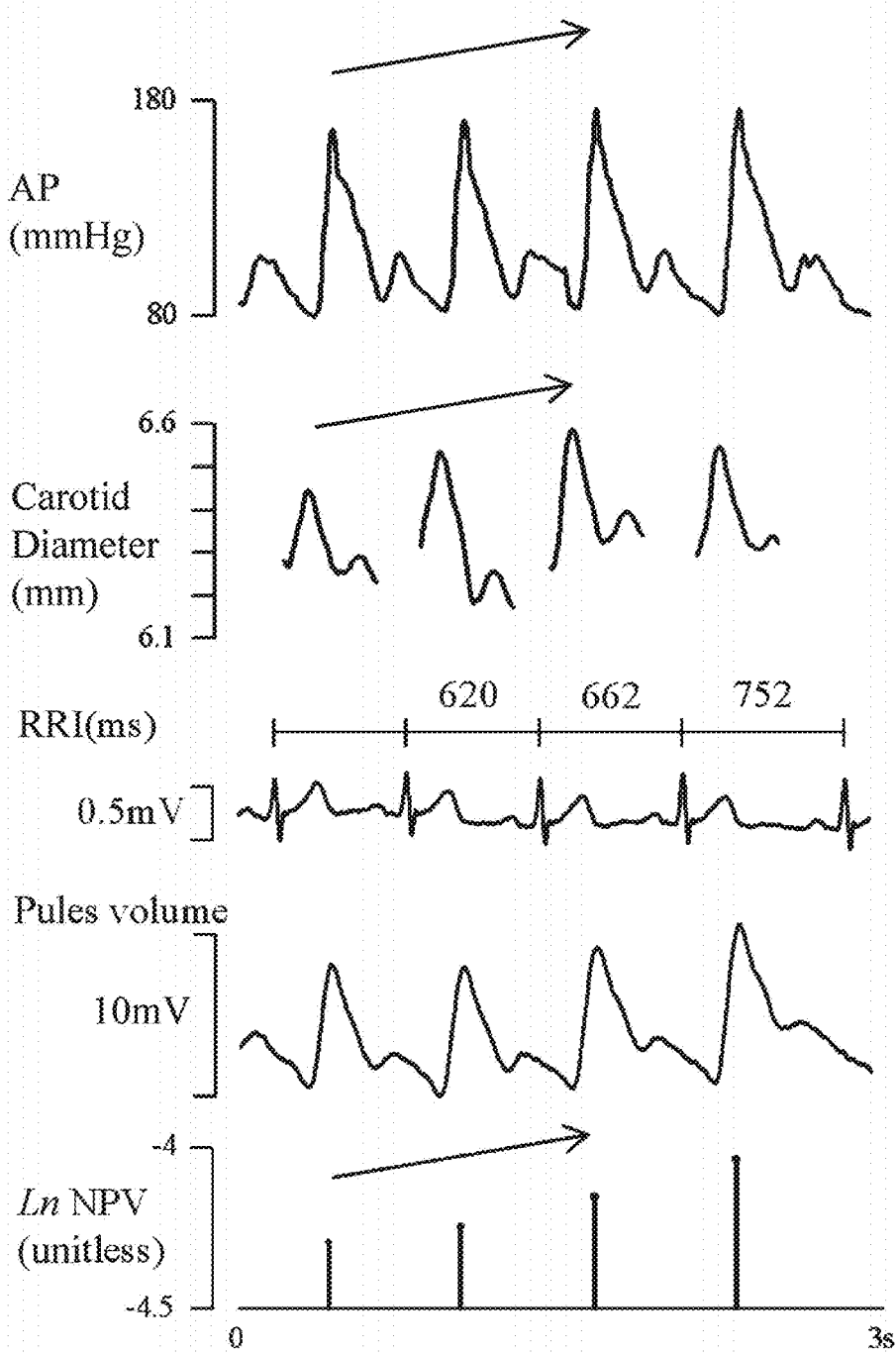
[FIG. 7]

[FIG. 8A]
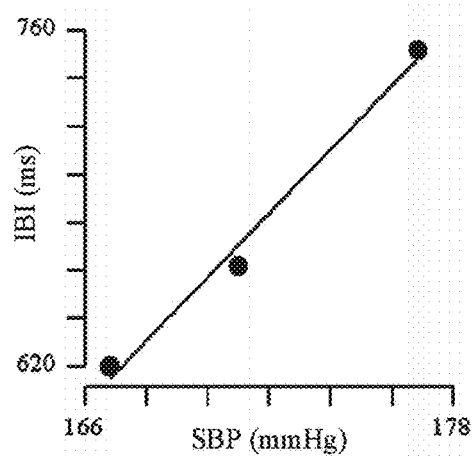
Int BRS = 13.3 ms/mmHg
[FIG. 8B]
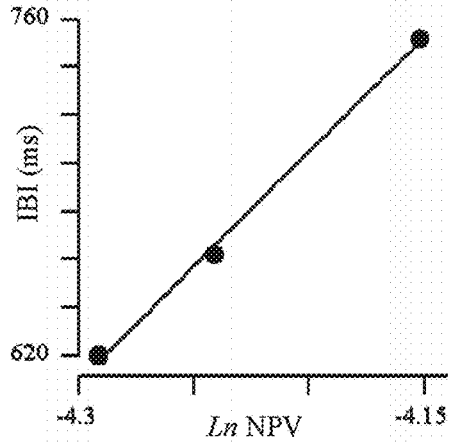
nBRS (NPV)= 952.2ms
[FIG. 8C]
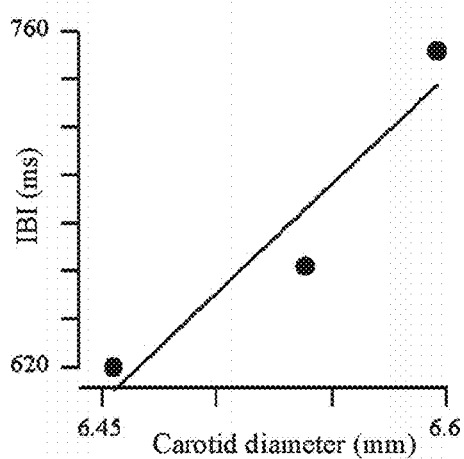
nBRS (D)= 713.9 ms/mm

[FIG. 9A]
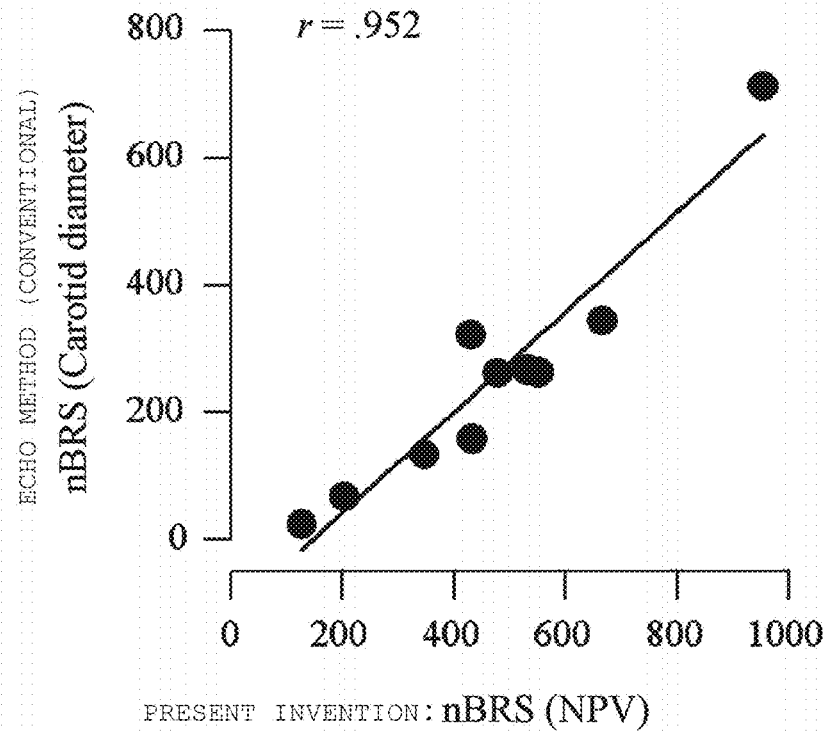
[FIG. 9B]
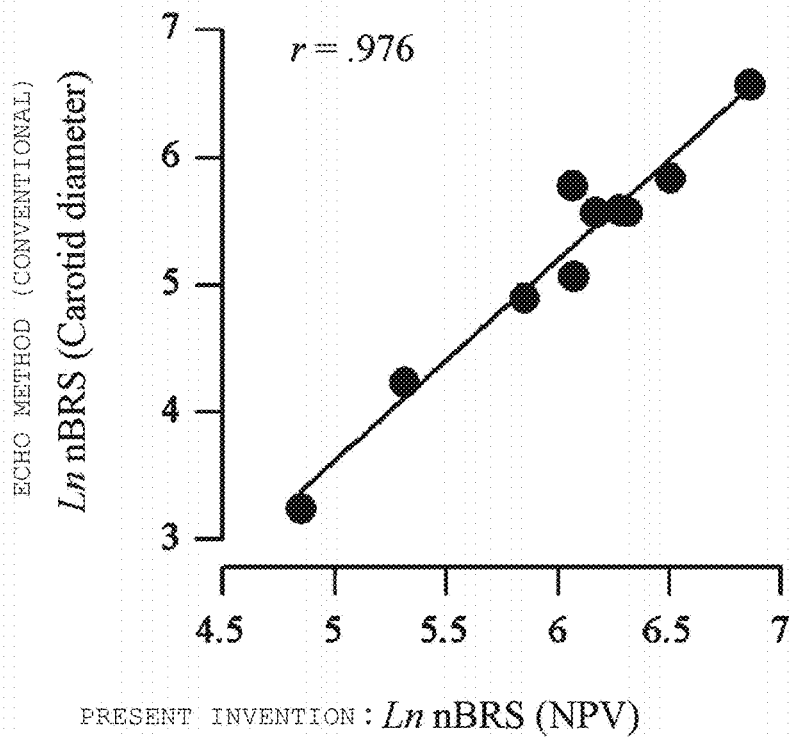

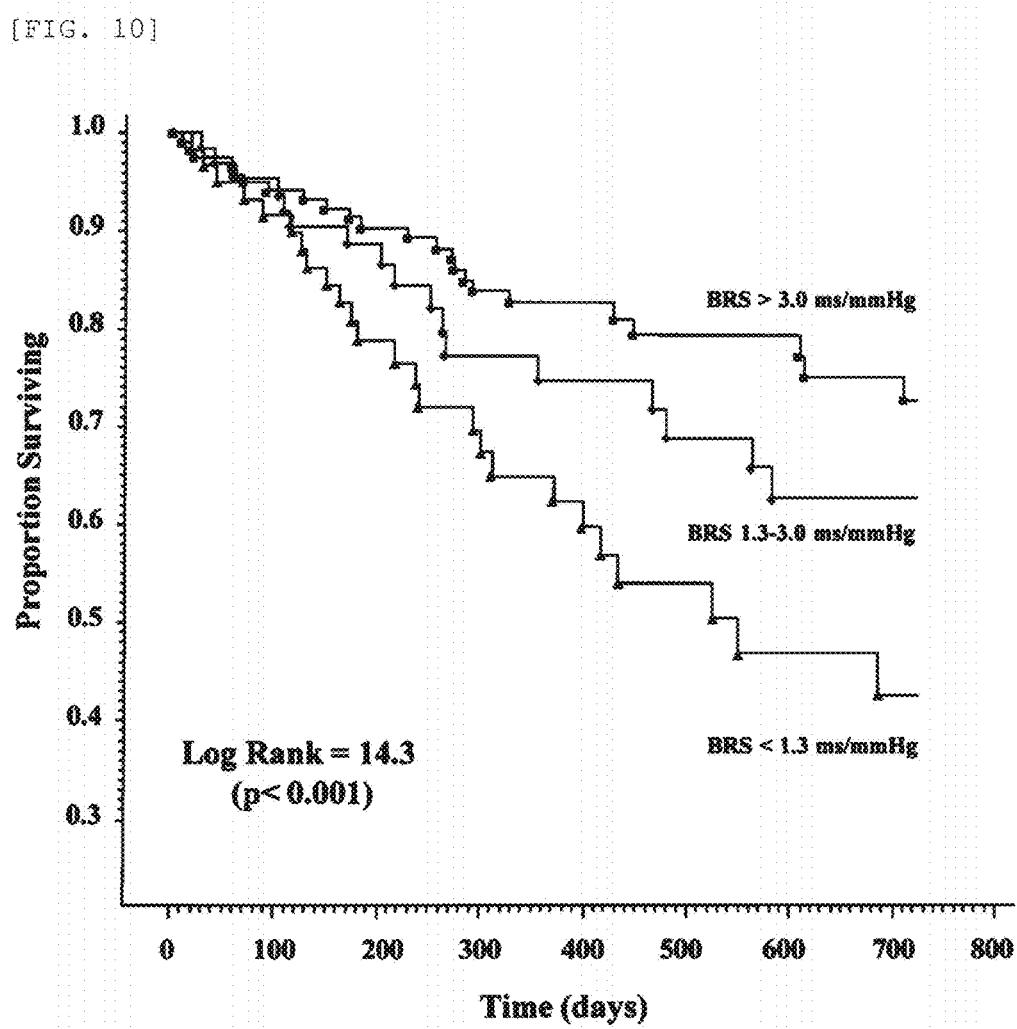
[FIG. 10]

NEUROGENIC BAROREFLEX SENSITIVITY MEASUREMENT DEVICE, NEUROGENIC BAROREFLEX SENSITIVITY MEASUREMENT PROGRAM AND NEUROGENIC BAROREFLEX SENSITIVITY MEASUREMENT METHOD

TECHNICAL FIELD

The present invention relates to a technique for measuring the sensitivity of a baroreflex function for keeping a blood pressure in a normal range and, more particularly, to a neurogenic baroreflex sensitivity measurement device, a neurogenic baroreflex sensitivity measurement program and a neurogenic baroreflex sensitivity measurement method suitable for measuring neurogenic baroreflex sensitivity that does not depend on the hardness of a blood vessel.

BACKGROUND ART

There has been known, as an autonomic nerve function related to blood pressure fluctuation, a baroreflex function for keeping a value of a blood pressure in a normal range. Deterioration in this baroreflex function is considered to cause hypertension or orthostatic hypotension. Therefore, a technique for measuring the sensitivity of the baroreflex function has been proposed. Specifically, there have been known a so-called intravenous injection method and a sequence method for measuring the sensitivity of the baroreflex function according to reflection sensitivity appearing as extension or reduction of a heartbeat interval (an RR interval) that occurs together with a rise or a drop of a blood pressure. There has also be proposed a method of measuring the baroreflex function on the basis of a relation between fluctuation in a blood pressure and fluctuation in a pulse wave propagation time involved in the fluctuation in the blood pressure (Patent Literature 1).

However, the aortic arch and the carotid baroreceptor serving as a base of the baroreflex function has a characteristic that the aortic arch and the carotid baroreceptor emit impulses according to stretch of a blood vessel wall. Therefore, as explained above, there is a problem in that the baroreflex sensitivity measured using the blood pressure depends on vascular stiffness and is not accurately measured. That is, there is a problem in that the baroreflex sensitivity calculated from the blood pressure is a result better than an actual value as the blood vessel is softer and is a result worse than the actual value as the blood vessel is harder.

In order to solve such problems, in recent years, there has also been proposed a method of measuring the baroreflex sensitivity on the basis of a correspondence relation of a heartbeat interval confirming a change in the blood vessel diameter by tracking and measuring a pulsation change of a blood vessel diameter in the carotid using an ultrasonic echo without using a blood pressure (Non Patent Literature 1: hereinafter referred to as "echo method"). According to this echo method, theoretically, it is possible to measure neurogenic baroreflex sensitivity that is not affected by a blood pressure and vascular stiffness.

CITATION LIST

Patent Literature

Patent Literature 1: Japanese Patent Application Laid-Open No. 2008-86568

Non Patent Literature

Non Patent Literature 1: Brian E. Hunt et al., "Quantification of Mechanical and Neural Components of Vagal Baroreflex in Humans, Hypertension, 2001, Vol. 37", p. 1362-1368, American Heart Association

SUMMARY OF INVENTION

Technical Problem

However, in the echo method, when the pulsation change of the blood vessel diameter in the carotid is measured, a patient needs to rest for a while in a state in which an ultrasonic probe is fixed to the neck of the patient. Therefore, for example, if the patient swallows saliva to move the throat even a little during a measurement, the measurement has to be performed again. It is difficult to measure an accurate pulsation change. Therefore, there is a problem in that the echo method is extremely unsuitable for clinical practice.

The present invention has been devised in order to solve such problems and it is an object of the present invention to provide a neurogenic baroreflex sensitivity measurement device, a neurogenic baroreflex sensitivity measurement program and a neurogenic baroreflex sensitivity measurement method that can simply and objectively measure, without using a blood pressure and a pulsation change of a blood vessel diameter in a carotid, neurogenic baroreflex sensitivity that does not depend on the hardness of a blood vessel.

Solution to Problem

A neurogenic baroreflex sensitivity measurement device according to the present invention includes: a pulse-wave-data acquiring unit that acquires pulse wave data of an artery; a normalized-pulse-volume calculating unit that calculates, on the basis of the pulse wave data, a normalized pulse volume obtained by dividing the amplitude of an alternating-current component of a pulse wave by an average of a direct-current component of the pulse wave at the same time; a beat-interval acquiring unit that acquires a beat interval corresponding to the pulse wave data; a baroreflex-series detecting unit that detects a baroreflex series in which both of the normalized pulse volume and the beat interval continuously increase or decrease for three beats or more; and a neurogenic-baroreflex-sensitivity calculating unit that calculates, as neurogenic baroreflex sensitivity that is an index indicating a neurogenic baroreflex function, a slope of a regression line indicating a correlation between the normalized pulse volume and the beat interval in the baroreflex series.

A neurogenic baroreflex sensitivity measurement program according to the present invention causes a computer to function as: a pulse-wave-data acquiring unit that acquires pulse wave data of an artery; a normalized-pulse-volume calculating unit that calculates, on the basis of the pulse wave data, a normalized pulse volume obtained by dividing the amplitude of an alternating-current component of a pulse wave by an average of a direct-current component of the pulse wave at the same time; a beat-interval acquiring unit that acquires a beat interval corresponding to the pulse wave data; a baroreflex-series detecting unit that detects a baroreflex series in which both of the normalized pulse volume and the beat interval continuously increase or decrease for three beats or more; and a neurogenic-baroreflex-sensitivity cal- culating unit that calculates, as neurogenic baroreflex sensitivity that is an index indicating a neurogenic baroreflex function, a slope of a regression line indicating a correlation between the normalized pulse volume and the beat interval in the baroreflex series.

A neurogenic baroreflex sensitivity measurement method according to the present invention includes: a pulse-wave-data acquiring step for acquiring pulse wave data of an artery; a normalized-pulse-volume calculating step for calculating, on the basis of the pulse wave data, a normalized pulse volume obtained by dividing the amplitude of an alternating-current component of a pulse wave by an average of a direct-current component of the pulse wave at the same time; a beat-interval acquiring step for acquiring a beat interval corresponding to the pulse wave data; a baroreflex-series detecting step for detecting a baroreflex series in which both of the normalized pulse volume and the beat interval continuously increase or decrease for three beats or more; and a neurogenic-baroreflex-sensitivity calculating step for calculating, as neurogenic baroreflex sensitivity that is an index indicating a neurogenic baroreflex function, a slope of a regression line indicating a correlation between the normalized pulse volume and the beat interval in the baroreflex series.

Advantageous Effects of Invention

According to the present invention, it is possible to simply and objectively measure, without using a blood pressure and a pulsation change of a blood vessel diameter in a carotid, neurogenic baroreflex sensitivity that does not depend on the hardness of a blood vessel.

BRIEF DESCRIPTION OF DRAWINGS

FIG. 1 is a block diagram showing an embodiment of a neurogenic baroreflex sensitivity measurement and a neurogenic baroreflex sensitivity measurement program according to the present invention.

FIG. 2 is a diagram for explaining a "beat interval" and a "beat interval corresponding to pulse wave data" according to the present invention.

FIG. 3 is a flowchart for explaining an embodiment of a neurogenic baroreflex sensitivity measurement method according to the present invention.

FIG. 4A is a diagram showing a state in which a photoplethysmogram of a finger artery is measured.

FIG. 4B is a sectional view of a fingertip showing a liquid layer through which light is transmitted.

FIG. 4C is a sectional view showing a fingertip in which only tissue components are different.

FIG. 5A is measured data of integrated baroreflex sensitivity (Int BRS), a systolic blood pressure (SBP), a heartbeat interval (RRI), a normalized pulse volume (NPV), and neurogenic baroreflex sensitivity (nBRS).

FIG. 5B is a diagram showing activity of the sympathetic nervous system in the finger artery.

FIG. 5C is a scatter diagram of the systolic blood pressure and NPV in the measured data in FIG. 5A.

FIG. 6 is a graph showing measured data in an example 1.

FIG. 7 is a graph of an example of a baroreflex series before and after approximately 80 seconds from a measurement start extracted from the measured data in FIG. 6.

FIG. 8A is a scatter diagram showing integrated baroreflex sensitivity (Int BRS) in the baroreflex series in FIG. 7.

FIG. 8B is a scatter diagram showing neurogenic baroreflex sensitivity (nBRS (NPV)) according to the present invention in the baroreflex series in FIG. 7.

FIG. 8C is a scatter diagram showing neurogenic baroreflex sensitivity (nBRS (D)) by an echo method in the baroreflex series in FIG. 7.

FIG. 9A is a graph showing a correlation between neurogenic baroreflex sensitivity (nBRS (NPV)) according to the present invention and neurogenic baroreflex sensitivity (nBRS (Carotid diameter)) by the echo method in an example 2.

FIG. 9B is a graph showing a correlation between natural logarithms (Ln) of the neurogenic baroreflex sensitivity (nBRS (NPV)) according to the present invention and natural logarithms (Ln) of the neurogenic baroreflex sensitivity (nBRS (Carotid diameter)) by the echo method in an example 2.

FIG. 10 is a graph showing a survival rate in future due to a difference in baroreflex sensitivity in a patient of a chronic heart failure.

DESCRIPTION OF EMBODIMENTS

A neurogenic baroreflex sensitivity measurement device, a neurogenic baroreflex sensitivity measurement program and a neurogenic baroreflex sensitivity measurement method according to the present invention are suitable for measuring neurogenic baroreflex sensitivity (nBRS), which is baroreflex sensitivity that does not depend on the hardness of a blood vessel.

As a result of earnest researches, the inventor found that it is possible to simply and objectively measure reliable neurogenic baroreflex sensitivity by using, instead of the blood vessel diameter of the carotid in the echo method explained above, a normalized pulse volume (hereinafter sometimes referred to as NPV) obtained by dividing the amplitude of an alternating-current component of a pulse wave in a finger artery by an average of a direct-current component of the pulse wave at the same time proposed in Japanese Patent No. 5039123.

An embodiment of the neurogenic baroreflex sensitivity measurement device, the neurogenic baroreflex sensitivity measurement program and the neurogenic baroreflex sensitivity measurement method according to the present invention is explained below with reference to the drawings.

As shown in FIG. 1, a neurogenic baroreflex sensitivity measurement device 1 in this embodiment mainly includes pulse-wave detecting means 2 for detecting a pulse wave of an artery, storing means 3 for storing a neurogenic baroreflex sensitivity measurement program 1a in this embodiment and various data, and arithmetic processing means 4 for controlling these constituent means, acquiring various data, and executing arithmetic processing. The constituent means are explained below in detail.

The pulse-wave detecting means 2 detects a volume pulse wave indicating a volume change in the artery. In this embodiment, the pulse-wave detecting means 2 includes a photo-sensor 21 that detects a light amount and a pulse wave amplifier 22 that amplifies an output signal from the photo-sensor 21 and outputs the output signal as pulse wave data. The photo-sensor 21 includes a light emitting unit 21a such as an LED (Light Emitting Diode) fixed to a nail of a finger and a light receiving unit 21b such as a photodiode disposed on the ball side of the finger in a position opposed to the light emitting unit 21a. The photo-sensor 21 detects, with the light receiving unit 21b, an amount of light emitted from the light emitting unit 21*a* and transmitted through the finger. The pulse wave amplifier 22 outputs the amplified pulse wave data in time series.

Note that, in this embodiment, photoplethysmogram data (FPG) is detected as the pulse wave data. In this embodiment, the finger artery is used as a detection target region of the pulse wave data. However, the detection target region is not limited to this. That is, the ear, the nose, the palm, the wrist, the neck, the arm, the foot, and the like can be set as the detection target region as long as a pulse wave of an artery can be detected by the pulse-wave detecting means 2 in the region.

Further, the pulse-wave detecting means 2 is not limited to the configuration explained above and only has to be means that can detect a pulse wave of an artery. For example, the pulse-wave detecting means 2 may be a wearable pulse wave sensor such as an earphone/earring type attachable to the ear, a bracelet type attachable to the wrist, the upper arm, or the like, or a ring type attachable to the finger. If such pulse-wave detecting means 2 is used, a burden in wearing the pulse-wave detecting means 2 is small. Further, detection in daily life is also possible.

The storing means 3 stores various data and functions as a working area when the arithmetic processing means 4 performs the arithmetic processing. In this embodiment, the storing means 3 is configured by a hard disk, a ROM (Read Only Memory), a RAM (Random Access Memory), a flash memory, and the like. As shown in FIG. 1, the storing means 3 includes a program storing unit 31 that stores the neurogenic baroreflex sensitivity measurement program 1*a* in this embodiment, a pulse-wave-data storing unit 32, a normalized-pulse-volume storing unit 33, a beat-interval storing unit 34, and an electrocardiogram-data storing unit 35.

In the program storing unit 31, the neurogenic baroreflex sensitivity measurement program 1*a* in this embodiment is installed. The neurogenic baroreflex sensitivity measurement program 1*a* is executed by the arithmetic processing means 4, whereby a computer such as a personal computer or a smart phone is caused to function as components explained below.

Note that a form of use of the neurogenic baroreflex sensitivity measurement program 1*a* is not limited to the configuration explained above. For example, the neurogenic baroreflex sensitivity measurement program 1*a* may be stored in a computer-readable recording medium such as a CD-ROM or a DVD-ROM, directly read out from the recording medium, and executed. The neurogenic baroreflex sensitivity measurement program 1*a* may be used from an external server or the like in an ASP (Application Service Provider) system or a cloud computing system.

The pulse-wave-data storing unit 32 stores the pulse wave data detected by the pulse-wave detecting means 2. The normalized-pulse-volume storing unit 33 stores a normalized pulse volume calculated by a normalized-pulse-volume calculating unit 42 explained below. The beat-interval storing unit 34 stores a beat interval acquired by a beat-interval acquiring unit 43 explained below. The electrocardiogram-data storing unit 35 stores electrocardiogram data obtained by electrocardiogram acquiring means (not shown in the figure) such as an electrocardiograph.

The arithmetic processing means 4 is configured from a CPU (Central Processing Unit) and the like. The arithmetic processing means 4 executes the neurogenic baroreflex sensitivity measurement program 1*a* to thereby function as a pulse-wave-data acquiring unit 41, a normalized-pulse-volume calculating unit 42, a beat-interval acquiring unit 43, a baroreflex-series detecting unit 44, and a neurogenic-baroreflex-sensitivity calculating unit 45. The components are explained more in detail below.

The pulse-wave-data acquiring unit 41 acquires the pulse wave data of the artery detected by the pulse-wave detecting means 2 and stores the pulse wave data in the pulse-wave-data storing unit 32 in time series. Note that, in this embodiment, the pulse-wave-data acquiring unit 41 directly acquires the pulse wave data from the pulse-wave detecting means 2. However, the pulse-wave-data acquiring unit 41 is not limited to this configuration. For example, the pulse-wave-data acquiring unit 41 may download pulse wave data measured by another device via the Internet or may capture pulse wave data into the pulse-wave-data storing unit 32 from a recording medium such as a USB memory.

The normalized-pulse-volume calculating unit 42 calculates the normalized pulse volume (NPV) explained above. Whereas the normalized pulse volume is evaluated by $\Delta I/I$, a transmitted light amount ($\Delta I$) equivalent to a pulsation change is determined by the amplitude of an alternating-current component of a pulse wave. A transmitted light amount ($I$) of a detection target region (a tissue+blood) of the pulse wave is determined by an average of a direct-current component of the pulse wave at the same time. Therefore, the normalized-pulse-volume calculating unit 42 divides, on the basis of the pulse wave data stored in the pulse-wave-data storing unit 32, the amplitude of the alternating-current component of the pulse wave by the average of the direct-current component of the pulse wave at the same time to thereby calculate the normalized pulse volume at every beat.

The beat-interval acquiring unit 43 acquires a beat interval corresponding to pulse wave data. In the present invention, as shown in FIG. 2, the "beat interval" is a concept including all time intervals equivalent to one beat of a beat such as a pulse interval in the pulse wave data (an interval of a period of a black star mark in FIG. 2), an interval of a rising portion of an alternating-current component of the pulse wave data (an interval in a period of a black circle mark in FIG. 2: hereinafter referred to as "rising interval"), and a heartbeat interval (an RR interval) in electrocardiogram data.

In the present invention, the "beat interval corresponding to pulse wave data" is a concept including not only a beat interval in a period of time same as a period of time when the pulse wave data is acquired but also a beat interval later by one beat than the period of time when the pulse wave data is acquired. Specifically, when the beat interval is a heartbeat interval, as shown in FIG. 2, not only heartbeat intervals a, b, and c but also heartbeat intervals b, c, and d correspond to the "beat interval corresponding to pulse wave data" with respect to pulse waves A, B, and C.

Therefore, in this embodiment, the beat-interval acquiring unit 43 refers to the pulse wave data stored in the pulse-wave-data storing unit 32 and acquires a pulse interval and a rising interval corresponding to the pulse wave data in time series. Note that, in this embodiment, in measurement for an aged person whose pulse interval and rising interval are less easily discriminated, electrocardiogram data is separately prepared in the electrocardiogram-data storing unit 35. In this case, the beat-interval acquiring unit 43 refers to the electrocardiogram data and acquires a heartbeat interval corresponding to the pulse wave data in time series.

The baroreflex-series detecting unit 44 detects a baroreflex series not affected by the sympathetic nervous system of a blood vessel. Specifically, the baroreflex-series detecting unit 44 refers to the normalized pulse volume in the normalized-pulse-volume storing unit 33 and the beat interval in the beat-interval storing unit 34 and detects, as the baroreflex series, a rising series in which both of the normalized pulse volume and the beat interval continuously increase for three beats or more or a falling series in which both of the normalized pulse volume and the beat interval continuously decrease for three beats or more.

The neurogenic-baroreflex-sensitivity calculating unit 45 calculates neurogenic baroreflex sensitivity, which is an index indicating a neurogenic baroreflex function. In this embodiment, the neurogenic-baroreflex-sensitivity calculating unit 45 acquires data of the baroreflex series detected by the baroreflex-series detecting unit 44 and calculates, as the neurogenic baroreflex sensitivity, a slope of a regression line indicating a correlation between the normalized pulse volume and the beat interval in the baroreflex series.

Note that, in this embodiment, the neurogenic baroreflex sensitivity measurement device 1 is configured by the personal computer including the storing means 3 and the arithmetic processing means 4. The pulse-wave detecting means 2 is separately connected as a peripheral device. However, a device configuration is not limited to the configuration explained above. For example, it is also possible to convert the neurogenic baroreflex sensitivity measurement program 1a in this embodiment into an application, install the neurogenic baroreflex sensitivity measurement program 1a in a smart phone, and cause the smart phone to function as the neurogenic baroreflex sensitivity measurement device 1 in this embodiment.

The action of the neurogenic baroreflex sensitivity measurement device 1 and the neurogenic baroreflex sensitivity measurement method executed by the neurogenic baroreflex sensitivity measurement program 1a in this embodiment are explained with reference to FIG. 3.

When neurogenic baroreflex sensitivity is measured using the neurogenic baroreflex sensitivity measurement device 1 in this embodiment, first, the pulse-wave-data acquiring unit 41 acquires pulse wave data (step S1: a pulse-wave-data acquiring step). Subsequently, the normalized-pulse-volume calculating unit 42 divides, on the basis of the pulse wave data acquired in step S1, the amplitude of an alternating-current component of a pulse wave by an average of a direct-current component of the pulse wave at the same time to thereby calculate a normalized pulse volume at every beat (step S2: a normalized-pulse-volume calculating step).

A merit of using the normalized pulse volume in calculating the neurogenic baroreflex sensitivity is explained. First, as shown in FIG. 4A, when a photoplethysmogram in a finger artery is measured using the light emitting unit 21a and the light receiving unit 21b, according to the Lambert-Beer's Law, absorption ($I/I_0$) at the time when light emitted from the light emitting unit 21a (a light amount $I_0$) passes a solution formed by one layer is proportional to the concentration (C) of the solution and the thickness (D) of the liquid layer. That is, if an average light absorption coefficient of arteries and veins is represented as $\epsilon$, the following Equation (1) holds:

$$I/I_0 = \exp(-\epsilon CD) \quad \text{Equation (1)}$$

On the other hand, as shown in FIG. 4B, as the liquid layer at the time when the light passes through a fingertip, a "non-pulsatile component" at the time when the artery is not beating, a "pulsatile component" at the time when the artery beats, and a "tissue component", which is a tissue of the finger are present. Therefore, as shown in FIG. 4C, when a trial calculation is performed concerning fingertips in which non-pulsatile components and pulsatile components are the same and only tissue components are different, a pulse volume ($PV = \Delta I$) is calculated larger in the fingertip in which the tissue component is smaller. On the other hand, as a normalized pulse volume ($NPV = \Delta I/I$), a correct pulsation change amount ($\Delta Va$) is calculated without being affected by a difference in the tissue component. That is, since the normalized pulse volume is a dimensionless absolute amount, the normalized pulse volume has a merit that not only comparison of measurement results acquired in different date and times concerning the same subject but also comparison between individuals is possible and, moreover, an error due to the tissue component of the fingertip is excluded.

Subsequently, when the beat-interval acquiring unit 43 acquires a beat interval corresponding to the pulse wave data (step S3: a beat-interval acquiring step), the baroreflex-series detecting unit 44 detects a baroreflex series in which both of the normalized pulse volume and the beat interval continuously increase or decrease for three beats or more (step S4: a baroreflex-series detecting step). Consequently, as explained below, a baroreflex series not affected by the sympathetic nervous system in the artery is specified.

Specifically, originally, in the artery, activity by the sympathetic nervous system is more predominant than in the carotid. Therefore, as shown in FIGS. 5A, 5B, and 5C, when the beat interval increases according to a sudden rise of the blood pressure, the blood vessel of the artery contracts according to an increase in the sympathetic nervous system activity. A blood amount represented by the normalized pulse volume decreases. Similarly, when the beat interval decreases according to a sudden drop of the blood pressure, the blood vessel of the artery expands according to a decrease in the sympathetic nervous system activity. The blood amount represented by the normalized pulse volume increases. Therefore, the inventor found that the influence of the sympathetic nervous system is excluded in an opposite series of above series, that is, a series in which both of the normalized pulse volume and the beat interval continuously increase or decrease and adopted the series as the baroreflex series according to the present invention.

Note that, in the present invention, the number of continuous beats detected as the baroreflex series is set to three beats or more in order to guarantee reliability that the baroreflex series is not affected by the sympathetic nervous system.

Finally, the neurogenic-baroreflex-sensitivity calculating unit 45 calculates, on the basis of the data of the baroreflex series detected by the baroreflex-series detecting unit 44, a slope of a regression line indicating a correlation between the normalized pulse volume and the beat interval in the baroreflex series as neurogenic baroreflex sensitivity (step S5). Consequently, the neurogenic baroreflex sensitivity is measured using the normalized pulse volume instead of the blood vessel diameter of the carotid in the echo method.

According to the present invention explained above, effects explained below are attained.

1. It is possible to simply and objectively measure neurogenic baroreflex sensitivity that does not depend on the hardness of a blood vessel without using a blood pressure and a pulsation change of a blood vessel diameter in a carotid.
2. It is possible to measure neurogenic baroreflex sensitivity not affected by a sympathetic nervous system in an artery and having high reliability.
3. By using a normalized pulse volume, which is a dimensionless absolute amount, an error due to a tissue component is excluded and not only comparison concerning the same subject but also comparison between individuals is possible. Therefore, it is possible to generally grasp a tendency of neurogenic baroreflex sensitivity.

4. It is possible to acquire an index of a parasympathetic nervous system from a baroreflex series. It is possible to acquire an index of a sympathetic nervous system from a series other than the baroreflex series.

5. By using the electrocardiogram data, it is possible to acquire an accurate beat interval even from a subject whose beat interval in a pulse wave is less easily read.

Subsequently, specific examples of the neurogenic baroreflex sensitivity measurement device 1, the neurogenic baroreflex sensitivity measurement program 1a, and the neurogenic baroreflex sensitivity measurement method according to the present invention are explained.

Example 1

In an example 1, an experiment for checking whether, in a finger artery in which pulse wave data was acquired, a baroreflex series not affected by a sympathetic nervous system was actually present was performed.

Specifically, a continuous blood pressure measurement device (device name: MUB101, manufacturer: Medisens Inc.), electrocardiogram detecting means (device name: LRR-03, manufacturer: GMS Co., Ltd.), and pulse-wave detecting means 2 (device name: MPN1001, manufacturer: Medisens Inc.) were attached to a subject (20 years old, male) to measure a blood pressure (AP), a heartbeat interval (RRI), and pulse wave data for 540 seconds in time series. At the same time, an ultrasonic probe (device name: UNEXEF38G, manufacturer: UNEX Corporation) was fixed to the neck of the subject to measure a diameter change (Carotid Diameter) in a carotid.

Measured data of these devices were processed by the neurogenic baroreflex sensitivity measurement device 1 in this embodiment and a UNEX EF (device name: UNEXEF38G, manufacturer: UNEX Corporation) to calculate integrated baroreflex sensitivity (Int BRS) by the conventional sequence method, neurogenic baroreflex sensitivity (nBRS (NPV)) according to the present invention, and neurogenic baroreflex sensitivity (nBRS (D)) by the conventional echo method. A result of this experiment is shown in FIG. 6.

Note that FIG. 7 is a graph of an example of a baroreflex series before and after approximately 80 seconds from a measurement start extracted from the measured data in FIG. 6. FIG. 8 is a scatter diagram in the baroreflex series in FIG. 7, wherein FIG. 8A is a diagram showing integrated baroreflex sensitivity (Int BRS) by the sequence method, FIG. 8B is a diagram showing neurogenic baroreflex sensitivity (nBRS (NPV)) according to the present invention, and FIG. 8C is a diagram showing neurogenic baroreflex sensitivity (nBRS (D)) by the echo method.

As shown in FIG. 6 to FIG. 8, it was indicated that sizes and frequencies of the baroreflex series according to the present invention are more than those in the baroreflex series in the conventional sequence method and the baroreflex series by the echo method in the past.

According to the example 1 explained above, it was verified that, in a finger artery in which pulse wave data is measured, the baroreflex series according to the present invention, that is, a baroreflex series in which both of a normalized pulse volume and a beat interval continuously increase or decrease for three beats or more and that is not affected by a sympathetic nervous is present.

Example 2

In an example 2, in the measured data in the example 1 shown in FIG. 6, relation concerning points where the neurogenic baroreflex sensitivity (nBRS (NPV)) according to the present invention and neurogenic baroreflex sensitivity (nBRS (Carotid diameter)) by the echo method could be simultaneously measured was evaluated. A result of the evaluation is shown in FIG. 9.

FIG. 9A is a graph showing a correlation between neurogenic baroreflex sensitivity according to the present invention and neurogenic baroreflex sensitivity by the echo method. FIG. 9B is a graph showing a correlation between natural logarithms (Ln) of the neurogenic baroreflex sensitivity according to the present invention and natural logarithms (Ln) of the neurogenic baroreflex sensitivity by the echo method. A correlation coefficient r in FIG. 9A was 0.952. The correlation coefficient r in FIG. 9B was 0.976. That is, in both the graphs, a high correlation was found between the neurogenic baroreflex sensitivity according to the present invention and the neurogenic baroreflex sensitivity by the echo method.

According to the example 2 explained above, since the high correlation was found between the neurogenic baroreflex sensitivity according to the present invention and the neurogenic baroreflex sensitivity by the echo method. It was verified that it is appropriate to use a normalized pulse volume instead of the blood vessel diameter of the carotid in the echo method.

Note that the neurogenic baroreflex sensitivity measurement device 1, the neurogenic baroreflex sensitivity measurement program 1a, and the neurogenic baroreflex sensitivity measurement method according to the present invention are not limited to the embodiment and the examples explained above and can be changed as appropriate.

For example, a display table (e.g., good, fair, bad) indicating evaluations of sensitivity of a baroreflex function in association with a numerical value range of neurogenic baroreflex sensitivity may be stored in the storing means 3. The evaluations concerning the sensitivity of the baroreflex function may be output from display means or printing means and presented to a subject on the basis of a value of the neurogenic baroreflex sensitivity calculated by the neurogenic-baroreflex-sensitivity calculating unit 45.

INDUSTRIAL APPLICABILITY

Conventionally, it has been known that, in a patient of a chronic heart failure, as shown in FIG. 10, deterioration in baroreflex sensitivity (a parasympathetic nerve function) is deeply related to a survival rate in future. Therefore, periodical measurement of neurogenic baroreflex sensitivity with high reliability is useful for disease predictions in a pre-clinical stage, screening, diagnoses, and long-term observations of all life-style related diseases including the chronic heart failure. Spreading effects to medical sites are extremely extensive.

As explained above, if the neurogenic baroreflex sensitivity measurement device 1 according to the present invention can be reduced in size to a portable terminal size of a smart phone and the like, the neurogenic baroreflex sensitivity measurement device 1 is considered to be widely spread for home use and personal use as health devices that can be easily handled by everyone from children to aged people.

REFERENCE SIGNS LIST

1 Neurogenic baroreflex sensitivity measurement device
1a Neurogenic baroreflex sensitivity measurement program
2 Pulse-wave detecting means
3 Storing means
4 Arithmetic processing means
21 photo-sensor
21a Light emitting unit
21b Light receiving unit
22 Pulse wave amplifier
31 Program storing unit
32 Pulse-wave-data storing unit
33 Normalized-pulse-volume storing unit
34 Beat-interval storing unit
35 Electrocardiogram-data storing unit
41 Pulse-wave-data acquiring unit
42 Normalized-pulse-volume calculating unit
43 Beat-interval acquiring unit
44 Baroreflex-series detecting unit
45 Neurogenic-baroreflex-sensitivity calculating unit

The invention claimed is:

1. A neurogenic baroreflex sensitivity measurement device comprising:
   a pulse-wave-data acquiring unit that acquires pulse wave data that indicates a volume change in an artery;
   a normalized-pulse-volume calculating unit that calculates, on the basis of the pulse wave data, a normalized pulse volume obtained by dividing amplitude of an alternating-current component of a pulse wave by an average of a direct-current component of the pulse wave at the same time;
   a beat-interval acquiring unit that acquires a beat interval corresponding to the pulse wave data;
   a baroreflex-series detecting unit that detects a baroreflex series in which both of the normalized pulse volume and the beat interval continuously increase or decrease for three beats or more; and
   a neurogenic-baroreflex-sensitivity calculating unit that calculates, as neurogenic baroreflex sensitivity that is an index indicating a neurogenic baroreflex function, a slope of a regression line indicating a correlation between the normalized pulse volume and the beat interval in the baroreflex series.

2. A non-transitory computer-readable recording medium storing a neurogenic baroreflex sensitivity measurement program that causes a computer to function as:
   a pulse-wave-data acquiring unit that acquires pulse wave data that indicates a volume change in an artery;
   a normalized-pulse-volume calculating unit that calculates, on the basis of the pulse wave data, a normalized pulse volume obtained by dividing amplitude of an alternating-current component of a pulse wave by an average of a direct-current component of the pulse wave at the same time;
   a beat-interval acquiring unit that acquires a beat interval corresponding to the pulse wave data;
   a baroreflex-series detecting unit that detects a baroreflex series in which both of the normalized pulse volume and the beat interval continuously increase or decrease for three beats or more; and
   a neurogenic-baroreflex-sensitivity calculating unit that calculates, as neurogenic baroreflex sensitivity that is an index indicating a neurogenic baroreflex function, a slope of a regression line indicating a correlation between the normalized pulse volume and the beat interval in the baroreflex series.

3. A neurogenic baroreflex sensitivity measurement method comprising:
   a pulse-wave-data acquiring step for acquiring pulse wave data that indicates a volume change in an artery;
   a normalized-pulse-volume calculating step for calculating, on the basis of the pulse wave data, a normalized pulse volume obtained by dividing amplitude of an alternating-current component of a pulse wave by an average of a direct-current component of the pulse wave at the same time;
   a beat-interval acquiring step for acquiring a beat interval corresponding to the pulse wave data;
   a baroreflex-series detecting step for detecting a baroreflex series in which both of the normalized pulse volume and the beat interval continuously increase or decrease for three beats or more; and
   a neurogenic-baroreflex-sensitivity calculating step for calculating, as neurogenic baroreflex sensitivity that is an index indicating a neurogenic baroreflex function, a slope of a regression line indicating a correlation between the normalized pulse volume and the beat interval in the baroreflex series.

4. The neurogenic baroreflex sensitivity measurement device according to claim 1, wherein the pulse-wave-data acquiring unit acquires, as the plus wave data, a volume pulse wave detected by a photo-sensor.

5. The non-transitory computer-readable recording medium according to claim 2, wherein the pulse-wave-data acquiring unit acquires, as the plus wave data, a volume pulse wave detected by a photo-sensor.

6. The neurogenic baroreflex sensitivity measurement method according to claim 3, wherein:
   in the pulse-wave-data acquiring step, a volume pulse wave detected by a photo-sensor is acquired as the pulse wave data.

* * * * *